United States Patent [19]

Crawford

[11] 4,180,511

[45] Dec. 25, 1979

[54] ASCORBIC ACID PROCESS

[75] Inventor: Thomas C. Crawford, Norwich, Conn.

[73] Assignee: Pfizer Inc., New York, N.Y.

[21] Appl. No.: 945,034

[22] Filed: Sep. 22, 1978

[51] Int. Cl.$^2$ .......................................... C07D 307/62
[52] U.S. Cl. .................................................. 260/343.7
[58] Field of Search ...................................... 260/343.7

[56] References Cited

U.S. PATENT DOCUMENTS 3,721,663  3/1973  Hinkley et al. ................... 260/343.7

*Primary Examiner*—Alan L. Rotman
*Assistant Examiner*—Robert C. Whittenbaugh
*Attorney, Agent, or Firm*—Francis X. Murphy; Charles J. Knuth; Peter C. Richardson

[57] ABSTRACT

An improved process for the preparation of ascorbic acid and erythorbic acid is disclosed, the improvement comprising the removal of borate impurities from a 2-ketogulonate and a 2-ketogluconate prior to formation of the desired acids by base catalyzed cyclization.

10 Claims, No Drawings

ASCORBIC ACID PROCESS

BACKGROUND OF THE INVENTION

The present invention relates to an improved process for the preparation of ascorbic and erythorbic acids. Ascorbic acid, or Vitamin C, is required in the human diet and is widely employed both in tablet form and as an additive in other foodstuffs to meet this need. Erythorbic acid, or isoascorbic acid, is useful as an antioxidant for use in foodstuffs.

Ascorbic acid has most commonly been prepared by a multi-step synthesis from D-glucose via sorbose and 2-ketogulonic acid, many improvements having been made to the original method of Reichstein and Grussner, Helv. Chim. Acta., 17, 311 (1934). Copending U.S. patent application Ser. No. 843,946 filed Oct. 20, 1977 describes a new route to ascorbic acid and erythorbic acid comprising the alkali metal borohydride reduction of 2,5-diketogluconic acid, or lower alkyl esters or salts of this acid, to form a mixture of 2-ketogulonic acid and 2-ketogluconic acid, or the corresponding esters or salts of these acids. The 2-ketogulonic acid is a precursor for ascorbic acid, while 2-ketogluconic acid is a precursor for erythorbic acid. The 2-keto acids are readily converted to the desired ascorbic and erythorbic acids by methods known in the art, for example by base catalyzed cyclization of the corresponding lower alkyl esters.

The borohydride reduction of 2,5-diketogluconic acid results in the presence of borate impurities in the reaction product containing the 2-keto acids. In accord with the present invention, it has now been discovered that the presence of such borate impurities in the 2-keto acid-containing reaction product results in lower yields of ascorbic and erythorbic acids when the corresponding alkyl esters are heated with a base to effect the cyclization to the desired final products.

SUMMARY OF THE INVENTION

The present invention therefore provides an improved process for the preparation of a compound selected from ascorbic acid and erythorbic acid which includes the steps of (a) reducing a compound selected from 2,5-diketogluconic acid, and n-alkyl ester of said acid, wherein the alkyl group has from 1 to 4 carbon atoms, and a salt of said acid selected from an alkali metal salt, an alkaline earth metal salt, an ammonium salt and a tetraalkyl ammonium salt having from 1 to 4 carbon atoms in each alkyl group, to form a reaction product containing borate impurities and, when said compound is selected from 2,5-diketogluconic acid and said salts of said acid, esterifying said reaction product; and (b) heating the product of step (a) in the presence of a base, the improvement which comprises the step of removing said borate impurities prior to said heating step.

In one process of interest, the borate impurities are removed as a trialkyl borate-n-alkyl alcohol azeotrope, wherein each alkyl group is of 1 to 3 carbon atoms, preferably methyl. The azeotrope is preferably formed by concentrating the borate impurity containing reaction product to a solid, dissolving the solid in an n-alkyl alcohol of 1 to 3 carbon atoms, preferably methanol, and heating the solution to reflux temperature in the presence of a catalytically-effective amount of a strong acid, preferably an acid selected from hydrochloric acid, sulfuric acid, paratoluene sulfonic acid and phosphoric acid.

In a second embodiment, the borate impurities are removed by addition of an alkali metal fluoride to the borate-containing reaction product, followed by contacting the resulting solution with a quaternary ammonium anion-exchange resin. A preferred alkali metal fluoride is sodium fluoride.

The borate impurities may also be removed directly from the borohydride reduction reaction product by contacting the reaction mixture with a borate-adsorbing solid adsorbent. A borate-specific resin adsorbent is a preferred adsorption medium, particularly at a pH of about 1 to 7.

DETAILED DESCRIPTION OF THE INVENTION

Copending U.S. patent application Ser. No. 843,946 filed Oct. 20, 1977 discloses a novel process for the preparation of mixtures of 2-ketogulonic acid and 2-ketogluconic acid by the alkali metal borohydride reduction of 2,5-diketogluconic acid, lower alkyl esters or salts thereof. Suitable esters include those having n-alkyl groups of 1 to 4 carbon atoms, preferably methyl. Suitable salts are those wherein the cation is an alkali metal, preferably sodium, an alkaline earth metal, preferably calcium, ammonium or tetraalkyl ammonium wherein each alkyl group is of 1 to 4 carbon atoms, preferably methyl. The reduction is effected by contacting the 2,5-diketogluconate starting material with about one equivalent, preferably 0.8 to 1.1 equivalents, of an alkali metal borohydride, when stereoselective and regioselective reduction of the 5-keto group results, thereby yielding a mixture of a 2-ketogulonate and a 2-ketogluconate, with the 2-ketogulonate being the predominant product. As used herein, 2-ketogulonate and 2-ketogluconate refers to the free acids and corresponding esters and salts thereof, the particular compound produced being dependent on the particular 2,5-diketogluconate starting material and the pH of the solution. The reduction is generally conducted in aqueous solution, optionally with organic cosolvents, at a pH above 5, preferably between about 6 and 10.5 at a temperature in the range −30° to 50° C., preferably about −25° C. to 25° C. If desired, the 2-ketogulonate and 2-ketogluconate present in the reduction reaction product may be separated from each other, for example by recrystallization or chromatography. Thus, either the mixture of 2-keto compounds or each of the isolated compounds separately can be subjected to further reactions as hereinafter described.

A by-product of the above described borohydride reduction reaction is boric acid, which may be present in the product mixture as hydrated boric oxides, borate salts, either ortho or meta borates, or as complexes thereof, depending on the cations present in the reaction solution and on the pH. In the specification and claims hereof, this by-product is referred to as "borate impurities" and it is intended that this should be understood to include such hydrated boric oxides, boric acid, borate salts or complexes, regardless of the particular form in which they may exist in the reaction solution.

The reaction product from the above reduction reaction, namely the 2-ketogulonate:2-ketogluconate mixture, can be readily converted to a mixture of ascorbic acid and erythorbic acid by means known in the art. Thus, the lower n-alkyl esters of 2-ketogulonic acid and 2-ketogluconic acid can be converted to ascorbic acid and erythorbic acid by heating in the presence of a base, such as an alkali metal carbonate, bicarbonate or hydroxide, preferably sodium carbonate or bicarbonate. The alkyl esters may be formed in the reduction reaction directly by employing the appropriate alkyl esters of 2,5-diketogluconic acid as a starting material. If 2,5-diketogluconic acid or a salt thereof is used as the substrate for the borohydride reduction, the reaction product must first be esterified, i.e. the alkyl esters of 2-ketogulonic acid and 2-ketogluconic acid must be formed in order to effect the subsequent base catalyzed cyclization reaction. As used in the claims and specification hereof the term esterified reaction product is meant to refer to the alkyl esters of 2-ketogulonic acid and 2-ketogluconic acid formed from the reaction product produced in the reduction of 2,5-diketogluconic acid and salts thereof, either as a mixture of the two esters or as the separated esters. The alkyl esters can be formed from the reduction reaction product, for example, by filtering the reaction mixture and adjusting the filtrate to a pH between about 1.5 and 2 and discarding any solid salts that are formed. The 2-ketogulonic acid and 2-ketogluconic acid can then be isolated by removing the reaction solvent, for example, by freeze drying or evaporation under reduced pressure. The acids may then be converted to the corresponding lower alkyl esters by heating the acids in an appropriate n-alkyl alcohol in the presence of an acid catalyst. Thus, for example, the methyl esters can be formed by heating the 2-keto acids in methanol in the presence of an acid catalyst such as hydrochloric acid, sulfuric acid, paratoluene sulfonic acid, sulfonic acid ion exchange resins, phosphoric acid and the like, for about 1 to 24 hours, preferably about 3 to 6 hours, depending on the temperature employed, reflux temperature being preferred. Other esters can be made by use of the appropriate n-alkyl alcohol. The above described reactions can be used to convert the mixture of 2-keto acids obtained from the initial reduction reaction to a mixture of the corresponding esters and also can be used to convert the acids when separated from each other to their respective esters.

The lower alkyl esters of 2-ketogulonic acid and 2-ketogluconic acid may be converted to ascorbic acid and erythorbic acid by refluxing in an organic solvent, typically a lower n-alkyl alcohol such as methanol, in the presence of a base, preferably sodium carbonate or bicarbonate, preferably in an inert atmosphere. If desired the alkyl esters of 2-ketogulonic acid and 2-ketogluconic acid can be separated and each converted to ascorbic acid and erythorbic acid respectively using the conditions described above. Ascorbic acid and erythorbic acid can be readily obtained from the resulting reaction solution. For example, when sodium bicarbonate is employed as the base, ascorbic acid and erythorbic acid are obtained as the corresponding sodium salts, which precipitate out on cooling. The crude salts are collected by filtration, mixed with water and deionized with a cation exchange resin such as Dowex 50 (Dow Chemical Co.). The water is removed and the ascorbic acid and erythorbic acid are recrystallized from methanol-water to give a mixture of ascorbic and erythorbic acids. If desired, ascorbic acid may be obtained by recrystallization from a suitable solvent, for example, 4:1 methanol-water solution.

It will be apparent from the above that the mixture of a 2-ketogulonate and a 2-ketogluconate can be employed to form a mixture of ascorbic acid and erythorbic acid. Alternatively, the 2-ketogulonate and the 2-ketogluconate can be separated from each other, either from the initial reduction product or from a mixture of the alkyl esters, and each can then be separately converted to the desired acid, i.e. to ascorbic acid and erythorbic acid respectively. It will be understood that all these embodiments are within the scope of the present invention and of the claims hereof.

It has now been found that the presence of the borate impurities formed as a by-product of the initial borohydride reduction adversely affect the yields of ascorbic acid and erythorbic acid obtained in the subsequent base catalysed cyclization of the alkyl esters of 2-ketogulonic acid and 2-ketogluconic acid. Further, it has been found that, in accord with the present invention, improved yields of ascorbic acid and erythorbic acid can be obtained by removing the borate impurities prior to the base catalyzed cyclization reaction. It should be understood that the borate impurities may be removed at any time subsequent to the completion of the reduction of the 2,5-diketogluconate starting material and prior to the step of heating the esters of 2-ketogulonic acid and 2-ketogluconic acid in the presence of a base. Thus, the borate impurities may be removed directly from the reduction reaction product or may be removed from the esterified reaction product. Further, the borate impurities may be removed either from mixtures of the 2-ketogulonate and 2-ketogluconate or from the isolated components thereof.

The borate impurities may be removed by a variety of methods, based on reactions and methods already known. In one method that is readily applicable to the present process, the borate impurities may be removed by converting them to a trialkyl borate, each alkyl group preferably being n-alkyl of 1 to 3 carbon atoms, most preferably methyl. The trialkyl borate is then conveniently removed from the reaction solution as the azeotrope formed with the corresponding n-alkyl alcohol, see for example Steinberg, Organoboron Chemistry, Volume I, page 38 et. seq., Interscience Publishers, New York, N.Y. (1964), U.S. Pat. No. 2,217,354, U.S. Pat. No. 2,813,115 and Schlesinger et. al., J.A.C.S., 75, 213 (1953). The trialkyl borate-n-alkyl alcohol azeotrope may be formed by concentrating the reduction product from the initial reduction reaction, or the esterified reaction product, to a solid. This may be effected, for example, by evaporating off the reaction solvent, preferably under reduced pressure or by concentration to about 50% solids followed by addition of an organic solvent at room temperature to precipitate the solids. The solids, which will be the 2-ketogulonate and 2-ketogluconate together with borate impurities, are then dissolved in the appropriate n-alkyl alcohol, preferably in methanol, which should be substantially free from water i.e. containing less than about 10% water. When the 2-ketogulonate and 2-ketogluconate are isolated as salts of the acid, about 1 equivalent of a strong acid such as hydrochloric acid, sulfuric acid, paratoluene sulfonic acid, phosphoric acid and the like, is added to aid dissolution of the solids in the alcohol solvent. The solution is then heated to reflux temperature in the presence of a catalytically effective amount of a strong acid such as hydrochloric acid, sulfuric acid, paratoluene sulfonic acid or phosphoric acid, reaction times of about 3 to 48 hours generally being required. As the heating proceeds, some of the n-alkyl alcohol is distilled off together with the trialkyl borate-n-alkyl alcohol azeotrope. In order to remove sufficient boron, more n-alkyl alcohol should be added to the reaction solution and the distillation process repeated several times i.e. 2 to 4 times. It is believed that some of the borate impurities may be complexed with the carbohydrate products and that such complexed borate impurities are in equilibrium with free borate impurities available for reaction to form the trialkyl borate. As the trialkyl borate-n-alkyl alcohol azeotrope is removed by distillation from the reaction vessel, dissociation of such complexed borate impurities will occur and further trialkyl borate will be formed and subsequently removed as the azeotrope by further distillation. Repeating this process several times will produce a substantially borate free solution of the alkyl esters for use in the further base catalyzed cyclization to ascorbic acid and erythorbic acid.

It will be understood that when the reaction product of the reduction process is isolated as the free acids or salts of the 2-ketogulonic acid and 2-ketogluonic acid, the above described reactions will be effective to both form the n-alkyl esters of the 2-keto acids required as starting material for the base catalyzed cyclization and to remove the borate impurities by formation of the trialkyl borate-n-alkyl alcohol azeotrope, with the formation of the esters proceeding at a greater rate than that for the removal of the trialkyl borate-n-alkyl alcohol azeotrope. Consequently, a suitable borate impurity free mixture of the esters of the 2-keto acids is obtained by heating the alcohol solution for time periods longer than those necessary merely to form the esters and by distilling off the trialkyl borate-n-alkyl azeotrope, together with some of the alcohol solvent, followed by addition of more alcohol to the reaction mixture and repeating this process several times in order to substantially reduce the borate impurity level in the ester solution.

The removal of borate impurities as the trialkyl borate-n-alkyl alcohol azeotrope is not limited to the above specifically described details and other means will be apparent to those skilled in the art. Thus, for example, the separation of the azeotrope may be effected by fractionation, chromatography or similar techniques and it is intended that such methods are to be considered as within the scope of the specification and claims hereof.

The borate impurities may also be removed from the reduction reaction product or the esterified reaction product by formation of an alkali metal tetrafluoroborate. The alkali metal tetrafluoroborate is formed by adding an alkali metal fluoride, preferably sodium fluoride, to the borate impurity containing mixture in an excess amount relative to the amount of borate impurities present. Preferably, between about 4 and 8 equivalents of sodium fluoride are added per equivalent of borate impurities, calculated as boric acid. The alkali metal tetrafluoroborate formed in this manner is readily removed from the reaction mixture, for example by contacting the reaction mixture containing the alkali metal tetrafluoroborate with a quaternary ammonium anion exchange resin. Suitable resins are well known in the art, an example of one such commercially available resin being IRA-900 (Rohm & Haas Co., Philadelphia, Pa.). The anion exchange resin may be added to the reaction mixture and after stirring for sufficient time to allow adsorption of the alkali metal tetrafluoroborate is removed by filtration. Preferably, the reaction solution containing the alkali metal tetrafluoroborate is passed over a column of the anion exchange resin, the resulting eluent being a substantially borate free mixture of the 2-ketogulonate and 2-ketogluconate ready for conversion to the corresponding alkyl esters, if necessary, and subsequent based catalyzed cyclization to ascorbic acid and erythorbic acid. The efficiency of the removal of the alkali metal tetrafluoroborate by the anion exchange resin is dependent on pH, with pH's between 1 and 5 being generally preferred.

The borate impurities may also be removed from the borohydride reduction reaction product or the esterified reaction product by adsorption on a borate-adsorbing solid adsorbent. Suitable solid adsorbents include silica gels, clays, starch and diatamaceous earths such as Celite (Johns-Manville). However, preferred adsorbents are certain resins that are specific for the adsorption of borate species of the type found in the present process, for example as described in U.S. Pat. No. 2,813,838, U.S. Pat. No. 3,856,670 and in Industrial and Engineering Chemistry, Product Research and Development, 3, 304 (1964). A commercially available resin of particular utility in the present process is Amberlite XE-243 (Rohm & Haas Co., Philadelphia, Pa.). The adsorbent may be added to the borate impurity-containing reaction product and stirred for sufficient time to allow adsorption of the borate impurities followed by removal of the resin by filtration. Preferably, the reaction product is passed over a column of the borate-specific adsorbent resin. Preferably, the pH of the reaction solution is maintained at between about 1 and 7, most preferably between about 1 and 5. When the borate-impurities are removed in this manner from a solution containing the free 2-ketogulonic and 2-ketogluconic acids, it is also preferable to pretreat the ion-exchange resin with acid, such as hydrochloric or sulfuric acid, such that the 2-keto acids are not adsorbed on the resin column.

The present invention is illustrated by the following examples. It should be understood, however, that the invention is not limited to the specific details of these examples.

EXAMPLE 1

The effect of the presence of borate impurities on the yield of ascorbic acid in the base catalyzed cyclization of methyl 2-ketogulonate was determined by the following procedure. To a 250 ml three-neck round bottom flask was added 50 ml of methanol and 5.0 g (24 mmol) of methyl 2-ketogulonate followed by 2.5 ml of water and 4.3 g (51 mmol) of sodium bicarbonate. The reaction was heated to reflux for 4 hours and concentrated to a dry solid. The yield of ascorbic acid, obtained as the sodium salt was determined by iodine titration.

The above procedure was repeated for reactions to which 1.5 g (24 mmol, 1 equivalent), 0.75 g (12 mmol, 0.5 equivalent) and 0.38 g (6 mmol, 0.25 equivalent) of boric acid had been added, respectively. The results obtained were as follows:

| Equivalents of Boric Acid in reaction solution | Yield of Ascorbic Acid, % |
|---|---|
| 0 | 92 |
| 1 | 11 |
| 0.5 | 43 |
| 0.25 | 61 |

EXAMPLE 2

The procedure of Example 1 was repeated for the base catalyzed cyclization of methyl 2-ketogluconate to erythorbic acid. The results obtained were as follows:

| Equivalents of Boric Acid in reaction solution | Yield of Erythorbic Acid, % |
| --- | --- |
| 0 | 89 |
| 1 | 4 |
| 0.5 | 43 |
| 0.25 | 58 |

EXAMPLE 3

To 200 ml of water was added 21.3 g (110 mmol) of 2-ketogulonic acid, 3.7 g (17 mmol) of sodium 2-ketogluconic acid, and 1.8 g (29 mmol) of boric acid. After adjusting the pH to 10.5 with 10% sodium hydroxide and then pH 6 with concentrated sulfuric acid, the solution was concentrated to a solid. This solid was slurried with 288 ml of methanol and 3.13 ml of concentrated sulfuric acid was added. The resulting sodium sulfate was removed by filtration and the reaction mixture heated to reflux for four hours. After cooling, 9.24 g of sodium bicarbonate was added and the resulting sodium sulfate removed by filtration. To the filtrate under nitrogen was added 41 g (488 mmol) of sodium bicarbonate and the reaction was heated to reflux for one hour. The reaction was cooled and filtered. The solid after drying weighed 37.6 g. Iodine titration showed that this material contained 8.8 mmol of ascorbic and erythorbic acids. The filtrate from the above solid was concentrated to afford 27.0 g of solid. Iodine titration showed that this material contained 60.9 mmol of ascorbic and erythorbic acids. The combined yield was 69.7 mmol or 57%.

The above reaction sequence was repeated using material to which no boric acid had been added. The overall yield was found to be 73% to a mixture of ascorbic and erythorbic acids.

EXAMPLE 4

To 2 liters of approximately 12.5% sodium 2,5-diketo-D-gluconate at 0° was added 10% sodium hydroxide to adjust the pH of the solution to 10.6. Sodium borohydride (10.4 g, 0.275 moles) was added. After 15 minutes the pH of the reaction mixture was 11.1 and was lowered to pH 6.6 by the addition of concentrated sulfuric acid. The final reaction volume was 2.15 l. An aliquot (215 ml) of the reaction mixture was freeze-dried and the resulting solid (32.1 g) was added to 300 ml of methanol containing 3.0 ml of concentrated sulfuric acid. After stirring for 0.5 hours, a tan solid was removed by filtration, and the filtrate was placed in a 500 ml three-neck Morton flask. To this was added 3.0 ml of concentrated sulfuric acid and methanol was distilled off by way of a short path distilling head. Before all the methanol had been removed an additional 300 ml of methanol was added and most of the methanol again removed by distillation. Another 300 ml of methanol was added followed by 9.63 g of sodium bicarbonate. After stirring for 15 minutes, the reaction mixture was filtered and the filtrate was transferred to a 500 ml Morton flask. After adding 38.5 g of sodium bicarbonate and 15 ml of water, the reaction mixture was heated to reflux for 5.3 hours. The solution was concentrated and the resulting solid was dried under vacuum to afford 56 g of a tan solid. Titration of 0.43 g of this solid with 0.1 N iodine solution (11.0 ml) demonstrated that the yield of ascorbic and erythorbic acids was 62%. The ratio of ascorbic acid to erythorbic acid was determined to be approximately 83:17 by glpc of the pertrimethylsilylated derivatives of the acids (160°, 10 ft, 3% OV 210 on Gas Chrom Q).

EXAMPLE 5

To a 100 ml three-neck Morton flask was added 1 g (4.7 mmol) of 2-ketogulonic acid, 100 ml of methanol, 0.072 g (1.2 mmol, 0.25 equivalents) of boric acid, and 0.1 ml of concentrated hydrochloric acid. This solution was heated to reflux and methanol removed via a Dean-Stark trap. As the methanol was removed fresh methanol was added (100 ml). A total of 172 ml of methanol was removed via the Dean-Stark trap. The reaction mixture was concentrated and the remaining white solid (0.97 g) was shown by atomic absorption not to contain boric acid.

EXAMPLE 6

Following the procedure of Example 5, 1 g (4.7 mmol) of 2-ketogulonic acid was dissolved in 10 ml of methanol containing 0.072 g (1.2 mmol, 0.25 equivalents) of boric acid and 0.1 ml of concentrated hydrochloric acid. The methanol was distilled off using a short-path distillation column and replaced by 10 ml of methanol which was also distilled off. The residue (0.964 g) contained no boric acid by atomic absorption.

EXAMPLE 7

To 100 ml of water was added 5 g (23.5 mmol) of 2-ketogulonic acid, 0.36 g (5.9 mmol, 0.25 equivalents) of boric acid, and 1.98 g (23.5 mmol) of sodium bicarbonate. This solution was concentrated and the resulting solid added to 24.0 ml of methanol to form a heterogeneous reaction mixture. Concentrated sulfuric acid (0.63 ml) was added and the resulting solid was removed by filtration. An additional 0.63 ml of concentrated sulfuric acid was added and the reaction mixture, after being brought to 50 ml volume with methanol, was heated to reflux. Two 50 ml portions of methanol were removed by distillation, after which a fresh 50 ml aliquot of methanol was added to the reaction mixture. The reaction mixture was neutralized with sodium bicarbonate (1.98 g), filtered, and brought to 50 ml volume with methanol. Assay of a sample showed that there was no boric acid remaining. The methanol solution was concentrated and triturated with ethyl acetate to effect crystallization. The crystals of methyl 2-ketogulonate (4.09 g) were collected and dried.

EXAMPLE 8

To 200 ml of water was added 20 g (94.2 mmol) of 2-ketogulonic acid, 7.91 g (94.2 mmol) of sodium bicarbonate, and 1.46 g (23.6 mmol, 0.25 equivalents) of boric acid. Of this solution 100 ml was concentrated to a solid. This solid was added to 100 ml of methanol followed by 1.6 ml (35 mmol) of concentrated sulfuric acid. The resulting solid was removed by filtration and the filtrate was placed in a 500 ml three-neck Morton flask to which was added 1.25 ml of concentrated sulfuric acid. The solution was heated to reflux and 50 ml of methanol was distilled off then replaced with 50 ml of fresh methanol. This procedure was repeated three times, a total of 210 ml of methanol being distilled off. To the reaction mixture was added 3.956 g of sodium bicarbonate after which the solid was removed by filtration. The volume of the methanol solution was brought to 100 ml by adding methanol and the solution was transferred to a 500 ml three-neck Morton flask and 15.8 g of sodium bicarbonate was added. This solution was heated to reflux for 2 hours after which the reaction was cooled and concentrated to a solid (25.2 g). A 0.40 g sample of this solid was titrated with 11.1 ml of a 0.1 N iodine solution, indicating a 74% yield of ascorbic acid.

EXAMPLE 9

To 309 ml of water was added 40 g (188 mmol) of 2-ketogulonic acid and 2.92 g (47 mmol, 0.25 equivalents) of boric acid. The pH was adjusted to 10.5 with 10% sodium hydroxide then to 6.0 with concentrated sulfuric acid. This solution was then concentrated to a white solid (43 g). To 50 ml of methanol was added 10 g (43.8 mmol) of the above solid followed by 2.6 ml of concentrated sulfuric acid. After stirring for 15 minutes the solid was removed by filtration and the filtrate was added to a 250 ml three-neck round-bottom flask fitted with a mechanical stirrer and a Soxhlet extractor containing 23.5 ml of AG 1-X8 quaternary ammonium polystyrene resin in the hydroxide form (Dow Chemical Co., Midland, Mich.) in an extraction thimble. The solution was heated to reflux for 6 hours, cooled, and neutralized with 8.9 g of sodium bicarbonate. The solvent was filtered off. Atomic absorption analysis of the filtrate showed that greater than 90% of the boric acid had been removed. To this solution was added methanol to bring the volume to 100 ml, then 5 ml of water and 14.7 g of sodium bicarbonate.

The reaction mixture was heated to reflux for 30 minutes and cooled. The volume of the reaction was brought to 500 ml with water and a 25 ml aliquot was titrated with 32.8 ml of 0.1 N iodine solution. The yield of sodium ascorbate was 75%.

EXAMPLE 10

To a 10% aqueous solution of 2-ketogulonic acid was added 0.25 equivalents of boric acid and 1 equivalent of sodium fluoride (fluoride:boric acid ratio=4). The pH of different samples of this solution was adjusted and the resulting solutions passed through a column of IRA-900 quaternary ammonium anion-exchange resin in the chloride form (Rohm & Haas, Co., Philadelphia, Pa.). The percentage of boron removed from each solution was determined by atomic absorption. The results obtained were as follows:

| pH of solution | % Boron Removed |
| --- | --- |
| 1.9 | 66 |
| 3.0 | 80 |
| 4.0 | 87 |
| 5.0 | 67 |
| 6.0 | 45 |
| 7.0 | 34 |
| 8.0 | 34 |
| 9.0 | 43 |

EXAMPLE 11

2 equivalents of sodium fluoride was added to a 10% aqueous solution of 2-ketogulonic acid containing 0.25 equivalents of boric acid (fluoride to boric acid ratio=8). The pH of various samples of this solution were carefully adjusted and the resulting solutions were passed down an IRA-900 anion exchange column in the chloride form (Rohm & Haas Co., Philadelphia, Pa.). The percentage of boron removed from each solution was determined by atomic absorption. The results obtained were as follows:

| pH of solution | % boron removed |
| --- | --- |
| 1.5 | 87 |
| 2.0 | 98 |
| 2.5 | 97 |
| 3.0 | 96 |
| 3.5 | 79 |
| 4.0 | 70 |
| 4.5 | 63 |
| 5.0 | 68 |
| 5.5 | 78 |

EXAMPLE 12

To 10 ml of 10% 2-ketogulonic acid containing 0.25 equivalents of boric acid at various pHs were added 4.4 g of Amberlite XE-243 resin (Rohm & Haas Co., Philadelphia, Pa.). After stirring for 1.5 hours the resin was removed by filtration and the solvent volume brought to 25 ml and the boron concentration determined by atomic absorption. The results are summarized below.

| pH of solution | % boron removed |
| --- | --- |
| 1.3 | 100 |
| 3 | 86 |
| 4 | 92 |
| 5 | 95 |
| 6.1 | 90 |
| 7 | 82 |
| 8.1 | 67 |
| 9.1 | 44 |

EXAMPLE 13

To a solution containing 103 ml of methanol, 2.5 ml of water, 1.4 ml of concentrated sulfuric acid, 0.70 g (11 mmol) of boric acid and 0.36 g (45 mmol) of methyl 2-ketogulonate was added 61 ml of Amberlite XE 243 resin (Rohm & Haas Co., Philadelphia, Pa.) previously washed with methanol. This solution was stirred at room temperature for 1 hour after which the resin was removed by filtration. Atomic absorption showed that greater than 85% of the boric acid was removed.

What is claimed is:

1. In a process for the preparation of a compound selected from ascorbic acid and erythorbic acid which includes the steps of (a) reducing a compound selected from 2,5-diketogluconic acid, an n-alkyl ester of said acid wherein the alkyl group has from 1 to 4 carbon atoms and a salt of said acid selected from an alkali metal salt, an alkaline earth metal salt, an ammonium salt and a tetraalkylammonium salt having from 1 to 4 carbon atoms in each alkyl group, to form a reaction product containing borate impurities and, when said compound is selected from 2,5-diketogluconic acid and said salts of said acid, esterifying said reaction product; and (b) heating the product of step (a) in the presence of a base, the improvement which comprises the step of removing said borate impurities prior to said heating step.

2. A process according to claim 1 wherein said borate impurities are removed as a trialkyl borate-n-alkyl alcohol azeotrope, wherein each alkyl group is of 1 to 3 carbon atoms.

3. A process according to claim 2 wherein said azeotrope is formed by concentrating said reaction product or said esterified reaction product to a solid, dissolving said solid in said n-alkyl alcohol and heating the resulting solution to the reflux temperature of said alcohol in the presence of a catalytically-effective amount of an acid selected from the group consisting of hydrochloric acid, sulfuric acid, p-toluenesulfonic acid and phosphoric acid.

4. A process according to claim 3 wherein each alkyl group is methyl.

5. A process according to claim 1 wherein said borate residue is removed by adding an alkali metal fluoride to said reaction product or to said esterified reaction product and contacting the product with a quaternary ammonium anion exchange resin.

6. A process according to claim 5 wherein the alkali metal is sodium.

7. A process according to claim 5 wherein the contacting is at a pH between about 1 to 5.

8. A process according to claim 1 wherein said borate impurities are removed by contacting said reaction product or said esterified reaction products with a borate-adsorbing solid adsorbent.

9. A process according to claim 8 wherein said solid adsorbent is a borate-specific resin adsorbent.

10. A process according to claim 9 wherein said contacting is conducted at a pH between about 1 to 7.

* * * * *